United States Patent [19]

Kapoor

[11] 4,180,679
[45] Dec. 25, 1979

[54] NOVEL SUBSTITUTED DINITROTOLUENES AND METHODS FOR PREPARING THE SAME

[75] Inventor: Inder P. Kapoor, Pennington, N.J.

[73] Assignee: American Cyanamid Company, Stamford, Conn.

[21] Appl. No.: 935,820

[22] Filed: Aug. 22, 1978

[51] Int. Cl.² .............................................. C07C 43/20
[52] U.S. Cl. ...................................... 568/583; 71/125; 260/577; 260/646; 562/437; 568/586; 568/705
[58] Field of Search ................ 260/646; 568/583, 585, 568/586, 588; 71/125

[56] References Cited

U.S. PATENT DOCUMENTS

| | | | |
|---|---|---|---|
| 2,587,566 | 2/1952 | Buc et al. | 568/583 |
| 2,768,217 | 10/1956 | Easton | 260/646 |

Primary Examiner—Leland A. Sebastian
Attorney, Agent, or Firm—Harry H. Kline

[57] ABSTRACT

There are provided substituted dinitrotoluenes and methods of preparation thereof, said dinitrotoluenes being useful as intermediates for the preparation of certain herbicidal 2,6-dinitroanilines.

10 Claims, No Drawings

NOVEL SUBSTITUTED DINITROTOLUENES AND METHODS FOR PREPARING THE SAME

The present invention relates to substituted dinitroluenes. More particularly, it relates to certain dinitrotoluenes having the structure:

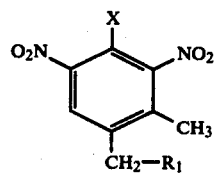
(I)

wherein X is selected from bromine, chlorine and iodine; $R_1$ is bromine or $-OR_2$; $R_2$ is alkyl $C_1-C_4$, hydroxyalkyl $C_1-C_4$ or phenyl.

A preferred group of compounds represented by formula (I) above-defined are those wherein $R_1$ is as hereinabove defined; $R_2$ is selected from $CH_3$, $C_2H_5$ and $C_2H_4OH$; and X is chlorine.

In general, the compounds of hereinabove formula (I) can be readily prepared by a reaction sequence schematically illustrated as follows:

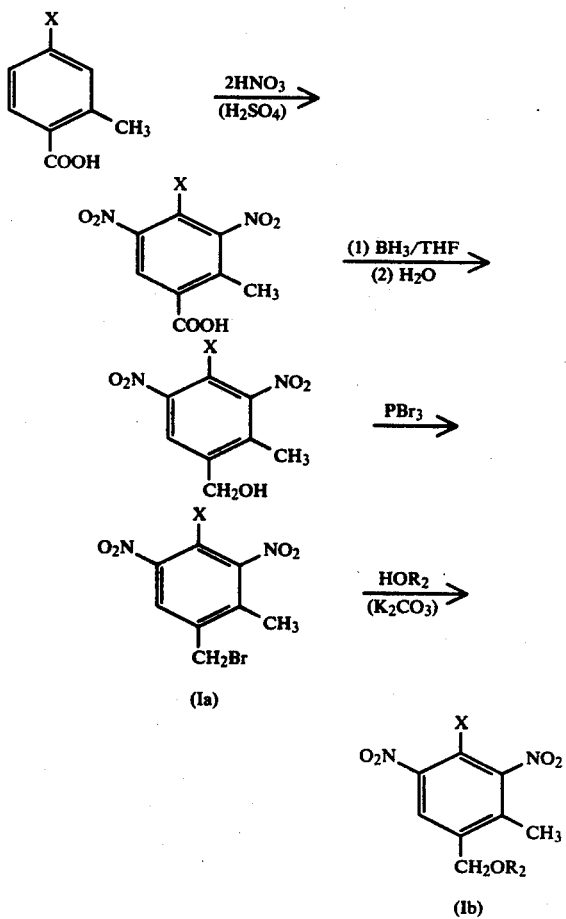

wherein formula (Ia) represents a compound of formula (I) above in which $R_1$ is bromine; and formula (Ib) represents a compound of formula (I) above in which $R_1$ is $OR_2$, and $R_2$ is as hereinabove defined.

Thus, for instance, 4-chloro-o-toluic acid is reacted with a mixture of concentrated nitric acid and sulfuric acid at a temperature range from about 40° C. to about 60° C. for a period of time from about 4 to 8 hours to yield the desired 4-chloro-3,5-dinitro-o-toluic acid. Reduction of the latter acid with diborane at room temperature in the presence of an inert solvent such as tetrahydrofuran (THF) under a blanket of inert gas such as nitrogen affords 4-chloro-2-methyl-3,5-dinitrobenzyl alcohol. Treating the so-obtained benzyl alcohol with phosphorus tribromide in the presence of an inert solvent such as benzene, toluene or xylene, at a temperature range from about 60° C. to 120° C. for from about three to six hours, yields the compound of formula (Ia). Finally, the compound of formula (Ia) $\alpha'$-bromo-4-chloro-3,5-dinitro-o-xylene is reacted with the appropriate aliphatic alcohol in the presence of an acid acceptor, such as sodium or potassium carbonate, at a temperature ranging from about 25° C. to about 80° C., for from one to eight hours, or until there is obtained a compound of formula (Ib):

wherein x is chlorine; $R_2$ is alkyl $C_1-C_4$, hydroxyalkyl $C_1-C_4$, or phenyl; and preferably, $R_2$ is $CH_3$, $C_2H_5$ or $C_2H_4OH$.

Formula (Ib) compounds are utilized in the preparation of dinitroaniline herbicides represented by formula (II):

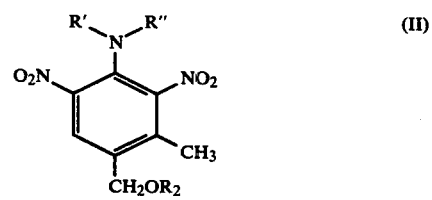
(II)

wherein R' is selected from hydrogen or alkyl $C_1-C_4$; R" is selected from alkyl $C_1-C_7$, cycloalkyl $C_3-C_7$ and monosubstituted alkyl $C_1-C_4$; where the substituent is selected from halogen and alkoxy $C_1-C_4$; $R_2$ is as hereinabove defined.

Advantageously, formula (II) compounds can be prepared from formula (Ib) compounds by nucleophilic substitution of the 1-halo group (X) with the appropriate amine. The nucleophilic substitution may be conducted from about 50° C. to 150° C., with or without an inert organic solvent, such as benzene, toluene and xylene.

The reaction is carried out by heating the reactants, preferably between 80° C. and 120° C, as graphically illustrated below:

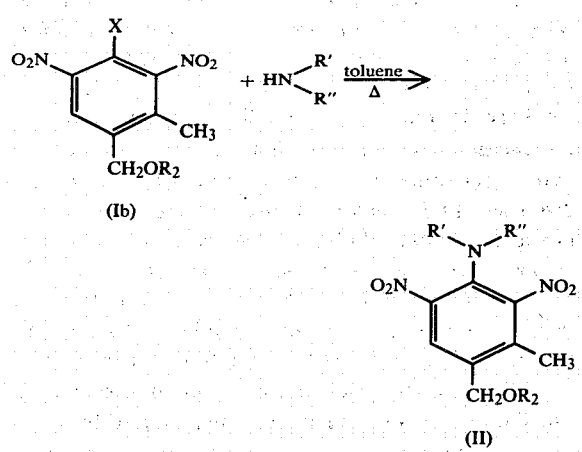

wherein X, R', R" and $R_2$ are as hereinabove defined.

Compounds represented by formula (II) can be used for the control of undesirable plant species. For such purpose, said compounds are usually formulated as solid or liquid herbicidal compositions, comprising an effective amount of a compound of formula (II) with a herbicidal adjuvant; i.e., an inert carrier and/or other conventional formulation aids.

Typical formulations include, for example, dusts, dust concentrates, wettable powders, granular compositions, flowable concentrates, emulsifiable concentrates, and the like. Application of said formula (II) compounds for the control of undesirable plant species is usually made at rates of from about 0.28 kg/hectare to about 11.2 kg/hectare, and preferably 0.56 kg/hectare to 4.48 kg/hectare of active compound.

The present invention is further illustrated by the following examples which are not to be taken as limitative thereof.

EXAMPLE 1

Preparation of 4-Chloro-3,5-dinitro-o-toluic acid

Fuming nitric acid (90%; 50 ml, d=1.5; 1.19 mol) is added dropwise with stirring to fuming sulfuric acid (20%; 800 ml) while the temperature of the mixture is maintained at 40° C. with external cooling. After the addition is completed, the acid mixture is allowed to cool to 35° C., and is then warmed to 60° C. 4-Chloro-o-toluic acid (73.6 g; 0.43 mol) is added to the above nitration mixture in portions, at a rate to maintain the temperature of the reaction mixture at 55° C. with external heating. After the addition is completed, a brown solution forms. The reaction mixture is first allowed to cool to 50° C., and is then heated to 60° C. and held at that temperature for 5.5 hours. During heating, the color of the reaction mixture changes to red, and a finely dispersed solid precipitates. The reaction is periodically checked for completion by tlc (silica gel plates; eluent: acetic acid-acetone-chloroform mixture in a 1:3:6 ratio). The reaction mixture is cooled to room temperature after 5.5 hours and stirred overnight. Thin layer chromatography (tlc) indic tes the presence of a mono-nitro component in addition to the product. The reaction mixture is stirred and heated at 90° C. for 1.5 hours and then stirred overnight at room temperature.

The reaction mixture is poured on 8 liters of ice with stirring, allowed to stand 0.5 hour, and is then filtered. The thus-isolated crude product is washed well with water, mixed with toluene (500 ml) and the mixture azeotroped at reflux until all the water present (ca. 28 ml) is removed. Toluene (250 ml) is added, the mixture heated to near reflux and is then filtered. Immediately some crystals form in the filtrate. The filtrate is cooled to 5° C., the solid isolated by filtration and air dried overnight to afford 82.0 g (73%) of title product as cream-colored crystals, melting point 189°–192° C.

EXAMPLE 2

Preparation of 4-Chloro-2-methyl-3,5-dinitrobenzyl alcohol.

4-Chloro-2-methyl-3,5-dinitrobenzoic acid (10.42 g; 0.04 mol) and dry tetrahydrofuran (THF; 50 ml) are charged to a reaction vessel from which the air was displaced by nitrogen gas under positive pressure. The thus-established nitrogen atmosphere is maintained throughout the reaction. A straw-colored solution forms. The solution is stirred and a 1 M solution of diborane in THF (42 ml, 0.042 mol) is added dropwise in 0.5 hour. Gas evolution occurs during addition of the first 30 ml of diborane solution and a slight exotherm is noted. The reaction mixture becomes colorless and a fine, white gelatinous solid forms. After 4 hours of stirring, the gelatinous solid dissolves, and the solution becomes straw-colored.

The completion of the reaction is followed by tlc. A representative aliquot is removed periodically from the reaction mixture, and is poured carefully on water. The precipitated solid is isolated and dissolved in ethyl acetate without drying and the solution spotted on a tlc plate (silica gel; eluent: methanol-methylene chloride in a ratio of 25:75 or a mixture of chloroform-acetone-acetic acid in a ratio of 6:3:1). After 60 hours, the reaction is complete and only one spot is found on the tlc plate.

The reaction mixture is stirred vigorously and water (250 ml) is added dropwise. No gas evolution is noted, but the mixture exotherms from 25° C. to 29° C. During the initial stages of water addition a fine, white, gelatinous solid forms and then dissolves as more water is added. The volume of the solution is adjusted to 600 ml with water. The mixture is stirred for 15 minutes, filtered and the solids washed well with water. The solids are dried to constant weight at 50°–55:C. in vacuo to afford 9.4 g (95.3%) of cream-colored crystalline solid, melting point 158°–160° C.

EXAMPLE 3

A. Preparation of α'-Bromo-4-chloro-3,5-dinitro-o-xylene

Phosphorus tribromide (18.0 g; 0.067 mol) is added dropwise at 10° C. to a stirred slurry of 4-chloro-2-methyl-3,5-dinitrobenzyl alcohol (50.0 g; 0.20 mol) in benzene (100 ml). The reaction mixture is allowed to warm to room temperature and then heated to reflux for 5 hours. After standing at room temperature overnight, the mixture is poured into water and extracted with ether. Insoluble material present is collected and dried to yield 18.9 g solid, melting point 115°–120° C. Removal of the ether from the extracts yields additional 38.6 g solid, melting point 106° C.–112° C.

B. Alternative Preparation of α'-Bromo-4-chloro-3,5-dinitro-o-xylene

A mixture of 4-chloro-3,5-dinitro-o-xylene (4.62 g; 0.02 mol), N-bromosuccinimide (3.90 g; 0.022 mol) and carbon tetrachloride (100 ml) is stirred and heated at reflux for 4 hours. The reaction mixture is then irradiated with a light source (60 watt) and refluxing continued for 2 hours. Next, 100 mg of initiator [2,2-azobis(2-methylpropionitrile)] is added and the mixture refluxed for one more hour. The reaction mixture is then cooled to room temperature and stirred under a light source for 48 hours, and filtered. The filtrate is evaporated to dryness in vacuo, and the solid residue recrystallized twice from ethanol to afford 1.35 g of title product.

EXAMPLE 4

Preparation of 4-Chloro-2-methyl-3,5-dinitrobenzyl methyl ether.

A warm solution of potassium carbonate (6.9 g; 0.05 mol) in water (20 ml) and methanol (50 ml) is added with stirring to a solution of α'-bromo-4-chloro-3,5-dinitro-o-xylene (15.5 g; 0.05 mol) in methanol (300 ml). The reaction mixture turns orange and a solid precipitates. After 30 minutes, the reaction is complete by glc analysis. The solids are removed by filtration and the filtrate concentrated in vacuo to a dark brown residue. The residue is treated with water and extracted with methylene chloride. The organic phase is washed with water, dried over magnesium sulfate, and concentrated in vacuo to afford 10.5 g (81%) of a dark orange oil, 91.2% pure by glc analysis. The product is chromatographed on activated magnesium silicate using chloroform as eluent. The initial fractions yield 7.4 g (57%) of product, a yellow semisolid.

Analysis calculated for $C_9H_9N_2O_5Cl$: C, 41.47; H, 3.48; N, 10.75; Cl, 13.60. Found: C, 41.43; H, 3.46; N, 10.70; Cl, 13.17.

By employing the above procedure, except ethylene glycol is substituted for methanol and heating the resultant solution at reflux, 2-(4-chloro-2-methyl-3,5-dinitrobenzyloxy)-ethanol is obtained.

EXAMPLE 5

Preparation of $\alpha^4$-Methoxy-N-(1-ethylpropyl)-2,6-dinitro-3,4-xylidine

3-Aminopentane (3.5 g; 0.004 mol) is added to a solution of 4-chloro-2-methyl-3,5-dinitrobenzyl methyl ether (0.4 g; $1.5 \times 10^{-3}$ mol) in toluene (20 ml). The solution is gently refluxed until tlc analysis of an aliquot (silica gel plate; eluent: methylene chloride-petroleum ether in a 65:35 ratio) indicates that the reaction is complete. The reaction mixture is cooled to room temperature and poured into 10% hydrochloric acid. The aqueous acidic phase is extracted with chloroform. The chloroform phase is dried over calcium sulfate and evaporated in vacuo to yield a yellow gum. Recrystallization from methanol affords 0.25 g (52%) of a bright yellow solid, melting point 48°–49.5° C.

Analysis calculated for $C_{14}H_{21}N_3O_5$: C, 54.01; H, 6.80; N, 13.50. Found: C, 53.84; H, 7.03; N, 13.50.

By the above procedure, but substituting cyclohexylamine for 3-aminopentane, $\alpha^4$-methoxy-N-cyclohexyl-2,6-dinitro-3,4-xylidine is obtained.

EXAMPLE 6

Preparation of $\alpha^4$-Methoxy-2,6-dinitro-N,N-dipropyl-3,4-xylidine.

Dipropylamine (4.08 g; 0.04 mol) and 4-chloro-2-methyl-3,5-dinitrobenzyl methyl ether (3.5 g; 0.013 mol) are dissolved in toluene (70 ml) and the solution heated at reflux for 46 hours. At the end of the first 28 hours, additional dipropylamine (1.3 g) is added to the reaction mixture since glc analysis indicates the presence of 11% starting material. After 46 hours at reflux, the reaction mixture is cooled, extracted with 2 N hydrochloric acid, the toluene phase is washed with water and dried over magnesium sulfate. The toluene phase is then concentrated in vacuo to yield 4.1 g of a dark oil. The crude product is purified by chromatography on silica gel using as eluent a gradient solution of 100% hexane to 70% hexane/30% benzene. The appropriate fractions containing the product the concentrated in vacuo to yield 2.1 g (50%) of a yellow-orange oil, found to be homogeneous by glc.

Analysis calculated for $C_{15}H_{23}N_3O_5$: C, 55.37; H, 7.12; N, 12.91. Found: C, 55.72; H, 7.42; N, 12.91.

EXAMPLE 7

Preparation of 4-Chloro-2-methyl-3,5-dinitrobenzyl ethyl ether.

Potassium carbonate (24.9 g; 0.18 mol) is added to a solution of α'-bromo-4-chloro-3,5-dinitro-o-xylene (5.1 g; 0.016 mol) in absolute ethanol (600 ml). The reaction mixture is stirred at room temperature for 3 hours, and filtered. The filtrate is concentrated in vacuo, the dark residue slurried in water and ethyl ether, the ether phase is separated and dried over magnesium sulfate. Removal of the ether leaves 3.0 g of a rust-colored material, which upon standing partially crystallizes to yield 2.7 g (61%) of a yellow solid.

By the above procedure, but using dry toluene as solvent and a 10 molar equivalent of phenol as reactant, and stirring the reaction mixture at 40°–50° C. until it is essentially complete, 4-chloro-2methyl-3,5-dinitrobenzyl phenyl ether is obtained.

EXAMPLE 8

Preparation of (−)-$\alpha^4$-Ethoxy-N[1-(methoxymethyl)propyl]-2,6-dinitro-3,4-xylidine.

A mixture of 4-chloro-2-methyl-3,5-dinitrobenzyl ethyl ether (2.7 g; 0.01 mol) and a 50% solution of (−)-1-(methoxymethyl)propylamine in tert-butanol (6.2 g; 0.03 mol) is stirred at room temperature overnight. Analysis by glc indicates the presence of 95% product. The reaction mixture is filtered, the filtrate washed with water, dilute acid then water, and dried over magnesium sulfate. Concentration in vacuo leaves 3.4 g of a dark oil, which is purified by chromatography on silica gel using toluene as eluent. Concentration of the toluene fractions in vacuo yield 1.4 g (41%) of an orange-colored oil, 99.1% pure by glc analysis.

Analysis calculated for $C_{15}H_{23}N_3O_6$: C, 52.78; H, 6.79; N, 12.30. Found: C, 53.17; H, 6.94; N, 12.25.

$[\alpha]_D^{25} = -0.787°$ (c 8.78, $CHCl_3$).

EXAMPLE 9

Preparation of 2-{{4-[(1-Ethylpropyl)amino]-2-methyl-3,5-dinitrobenzyl}oxy }ethanol.

3-Aminopentane (1.74 g; 0.02 mol) is added to a solution of 2-(4-chloro-2-methyl-3,5-dinitrobenzyloxy)ethanol (0.5 g; $1.7 \times 10^{-3}$ mol) in toluene. The reaction mixture is heated at reflux for 3 hours. Analysis by tlc (silica gel plate; eluent: methanol-benzene in a 1:9 ratio) shows the reaction to be complete. The reaction mixture is poured into 10% hydrochloric acid and extracted with methylene chloride. The organic phase is dried over calcium sulfate; and evaporated in vacuo to afford 0.54 g (91.8%) of an orange-colored oil.

Analysis calculated for $C_{15}H_{23}N_3O_6$: C, 52.78; H, 6.79; N, 12.31. Found: C, 52.86; H, 6.41; N, 12.28.

EXAMPLE 10

Evaluation of the Preemergence Herbicidal Activity of the Compounds of the Present Invention.

The preemergence herbicidal activity of the compounds of the present invention is demonstrated by the following tests in which the seeds of a variety of monocotyledonous and dicotyledonous plants are separately mixed with potting soil and planted on top of approximately 2.5 cm of soil in separate pint cups. After planting, the cups are sprayed with the selected aqueous acetone solution containing the test compound in sufficient quantity to provide the equivalent of about 0.146 kg to 11.2 kg per hectare of test compound per cup. The treated cups are then placed on greenhouse benches, watered and cared for in accordance with conventional greenhouse procedures. Three to five weeks after treatment, the tests are terminated and each cup is examined and rated according to the rating system set forth below. The test results obtained are reported in Table I below.

| Rating System | |
|---|---|
| Rating: | % Difference in Growth from the Check* |
| 0  No effect | 0 |
| 1  Possible effect | 1–10 |
| 2  Slight effect | 11–25 |
| 3  Moderate effect | 26–40 |
| 5  Definite injury | 41–60 |
| 6  Herbicidal effect | 61–75 |
| 7  Good herbicidal effect | 76–90 |
| 8  Approaching complete kill | 91–99 |
| 9  Complete kill | 100 |
| 4  Abnormal growth; i.e., a definite physiological malformation but with an over-all effect less than 5 on the rating scale. | |

*Based on visual determination of stand, size, vigor, chlorosis, growth malformation and over-all plant appearance.

Plant Abbreviations:
SE—Sesbania (*Sesbania exaltata*)
LA—Lambsquarters (*Chenopodium album*)
MU—Mustard (*Brassica kaber*)
PI—Pigweed (*Amaranthus retroflexus L.*)
RW—Ragweed (*Ambrosia artemisiifolia*)
MG—Morningglory (*Ipomoea purpurea L.*)
BA—Barnyardgrass (*Echinochloa crusgalli L.*)
CR—Crabgrass (*Digitaria sanguinalis L.*)
FO—Foxtail (*Setaria faberii*)
WO—Wild oats (*Avena fatua*)
VL—Velvetleaf (*Abutilon theophrasti*)
TW—Teaweed (*Sida spinosa*)
JW—Jimsonweed (*Datura stramonium L.*)
CN—Corn (*Zea mays*)
CO—Cotton (*Gossypium hirsutum*)
SY—Soybeans (*Glycine max*)
RI—Rice (*Oryza sativa L.*)

TABLE I

Evaluation of the Preemergence Herbicidal Activity of Amine Derivatives of the Compounds of the Present Invention
(The ratings are single values except as noted.)

| Compound | Rate: kg/Hectare | SE | LA | MU | PI | RW | MG | BA | CR | FO | WO | VL | TW | CN | CO | SY | RI |
|---|---|---|---|---|---|---|---|---|---|---|---|---|---|---|---|---|---|
| H—N—CH(C$_2$H$_5$)$_2$ / O$_2$N—[ring]—NO$_2$ / CH$_3$ / CH$_2$OCH$_3$ | 11.2 | 8 | | 9 | 9 | 9 | 9 | 9 | 9 | 9 | 7 | 8 | 8 | | | | |
| | 1.12 | 3 | 8 | 8 | 8* | 0 | 3* | 8.5* | 9* | 9* | 5 | 7* | 3 | 4* | 0* | 0* | 2 |
| | 0.56 | 0 | 8 | 2 | 7.5* | 0 | 0.5* | 8* | 9* | 8.5* | 0 | 4* | 0 | 0* | 0* | 0* | 1 |
| | 0.28 | 0 | 8 | 0 | 3.5* | 0 | 0* | 7* | 8.5* | 7.5* | 0 | 3.5* | 0 | 0* | 0* | 0* | 0 |
| | 0.146 | 0 | 8 | 0 | 2.5* | 0 | 0* | 7.5* | 7.5* | 7.0* | 0 | 0 | 0 | 0* | 0* | 0* | 0 |
| H—N—CH(C$_2$H$_5$)(CH$_2$OCH$_3$) / O$_2$N—[ring]—NO$_2$ / CH$_3$ / CH$_2$OCH$_3$ (—) | 11.2 | 7 | | 8 | 9 | 0 | 8 | 9 | 9 | 9 | 0 | 8 | 8 | | | | |
| | 1.12 | 0 | | 0 | 0 | 0 | 0 | 9 | 9 | 3 | 0 | 0 | 0 | 0 | 0 | 0 | |
| | 0.56 | 0 | | 0 | 0 | 0 | 0 | 6 | 8 | 0 | 0 | 0 | 0 | 0 | 0 | 0 | |
| | 0.28 | 0 | | 0 | 0 | 0 | 0 | 0 | 2 | 0 | 0 | 0 | 0 | 0 | 0 | 0 | |
| | 0.146 | 0 | | 0 | 0 | 0 | 0 | 0 | 0 | 0 | 0 | 0 | 0 | 0 | 0 | 0 | |
| N(C$_3$H$_7$-n)$_2$ / O$_2$N—[ring]—NO$_2$ / CH$_3$ / CH$_2$OCH$_3$ | 11.2 | 8 | | 8 | 9 | 0 | 8 | 9 | 9 | 9 | 4 | 7 | 8 | | | | |
| | 1.12 | 0 | | 0 | 6 | 0 | 0 | 5 | 9 | 9 | 0 | 2 | 5 | 0 | 0 | 0 | |
| | 0.56 | 0 | | 0 | 0 | 0 | 0 | 3 | 7 | 6 | 0 | 2 | 2 | 0 | 0 | 0 | |
| | 0.28 | 0 | | 0 | 0 | 0 | 0 | 1 | 6 | 6 | 0 | 0 | 1 | 0 | 0 | 0 | |
| | 0.146 | 0 | | 0 | 0 | 0 | 0 | 0 | 3 | 3 | 0 | 0 | 0 | 0 | 0 | 0 | |

TABLE I-continued

Evaluation of the Preemergence Herbicidal Activity of Amine Derivatives of the Compounds of the Present Invention
(The ratings are single values except as noted.)

| Compound | Rate: kg/Hectare | SE | LA | MU | PI | RW | MG | BA | CR | FO | WO | VL | TW | CN | CO | SY | RI |
|---|---|---|---|---|---|---|---|---|---|---|---|---|---|---|---|---|---|
| H—N—CH($C_2H_5$)$_2$ on 2,4-dinitro-3-methyl-6-(2-hydroxyethoxymethyl)phenyl ($O_2N$, $NO_2$, $CH_3$, $CH_2OCH_2CH_2OH$) | 11.2 | 8 | 0 | 4 | 0 | 1 | 8 | 9 | 9 | 0 | 4 | | | | | | |

*Average of two or more tests.

EXAMPLE 11

Evaluation of the Postemergence Herbicidal Activity of the Compounds of the Present Invention The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in 7 cm squares for about two weeks. The test compounds are dispersed in 50/50 acetone/water mixture in sufficient quantity to provide the equivalent of about 0.146 kg to 11.2 kg per hectare of active compound, when applied to the plants through a spray nozzle operating at 2.11 kg cm$^{-1}$ pressure for a predetermined time. After spraying, the plants are placed on greenhouse benches and are cared for in the usual manner, commensurate with conventional greenhouse practices. Three to five weeks after treatment, the seedling plants are examined and rated according to the rating system provided in Example 10. The herbicidal proficiency of the active compounds of the present invention is evident from the test results which are reported in Table II below.

TABLE II

Evaluation of the Postemergence Herbicidal Activity of Amine Derivatives of the Compounds of the Present Invention
(The ratings are single values except as noted.)

| Compound | Rate: kg/Hectare | SE | LA | MU | PI | RW | MG | BA | CR |
|---|---|---|---|---|---|---|---|---|---|
| H—N—CH($C_2H_5$)$_2$ on 2,4-dinitro-3-methyl-6-(methoxymethyl)phenyl ($O_2N$, $NO_2$, $CH_3$, $CH_2OCH_3$) | 11.2 | 6* | 0* | 6* | 6* | 2 | 4* | 6* | 6* |
| | 4.48 | | | 6 | | | 5 | 5 | 5 |
| | 2.24 | | 0 | | 1 | | 7 | 9 | 8 |
| | 1.12 | | 0 | 8 | 1 | | 5.5* | 6.5* | 6.5* |
| | 0.56 | | 0 | 8 | 0 | | 5.5* | 6.5* | 6.5* |
| | 0.28 | | 0 | 3 | 0 | | 5* | 4* | 5.5* |
| | 0.146 | | 0 | | | | 5 | 8 | 9 |
| H—N—CH($C_2H_5$)(CH$_2$OCH$_3$) on 2,4-dinitro-3-methyl-6-(methoxymethyl)phenyl (−) | 11.2 | 4 | 0 | 0 | 0 | 0 | 8 | 8 | 1 |
| | 4.48 | | 0 | | | | 5 | 1 | 0 |
| | 1.12 | | 0 | | | | 0 | 0 | 0 |
| N($C_3H_7$-n)$_2$ on 2,4-dinitro-3-methyl-6-(methoxymethyl)phenyl | 11.2 | 0 | | 0 | 0 | 0 | 0 | 4 | 4 |
| | 4.48 | | | 7 | | | 7 | 1 | 2 |
| | 1.12 | | | 2 | | | 3 | 0 | 0 |
| H—N—CH($C_2H_5$)$_2$ on 2,4-dinitro-3-methyl-6-(2-hydroxyethoxymethyl)phenyl ($CH_2OCH_2CH_2OH$) | 11.2 | 3 | 0 | 0 | 0 | 4 | 7 | 7 | |

TABLE II-continued
Evaluation of the Postemergence Herbicidal Activity of Amine Derivatives of the Compounds of the Present Invention
(The ratings are single values except as noted.)

| Compound | Rate: kg/Hectare | FO | WO | VL | TW | JW | CN | CO | SY | RI |
|---|---|---|---|---|---|---|---|---|---|---|
| 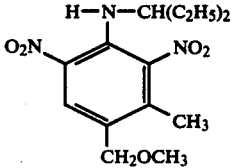 | 11.2 | 5.5* | 6.5* | 0 | 6* | | | | | |
| | 4.48 | 3 | 0 | 7 | 5 | | 0 | 5 | 3 | 2 |
| | 2.24 | 7 | 2 | 8 | 6 | 7 | 0 | 5 | 3 | 0 |
| | 1.12 | 4* | 0* | 6.5* | 6.5* | 7 | 0 | 5* | 3* | 0* |
| | 0.56 | 3.5* | 0* | 7* | 5.5* | 5 | 0* | 5* | 3* | 0* |
| | 0.28 | 3* | 0* | 6* | 5.5* | 3 | 0* | 5* | 3* | 0* |
| | 0.146 | 6 | 0 | 6 | 6 | 1 | 0 | 5 | 0 | 0 |
| 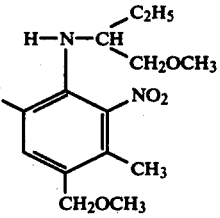 (−) | 11.2 | 1 | 6 | 4 | 4 | | | | | |
| | 4.48 | 0 | 0 | 5 | 2 | | 0 | 6 | 0 | 0 |
| | 1.12 | 0 | 0 | 2 | 2 | | 0 | 2 | 0 | 0 |
| 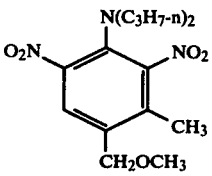 | 11.2 | 4 | 0 | 4 | 2 | | | | | |
| | 4.48 | 3 | 0 | 7 | 5 | | 0 | 4 | 0 | 0 |
| | 1.12 | 0 | 0 | 5 | 3 | | 0 | 4 | 0 | 0 |
| 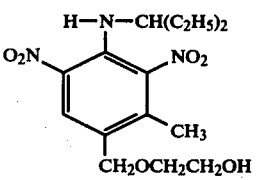 | 11.2 | 1 | 7 | 4 | | | | | | |

*Average of two or more tests.

I claim:

1. A compound of the formula:

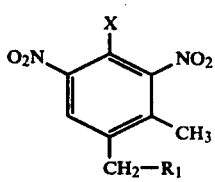

wherein X is halogen; $R_1$ is a member selected from the group consisting of bromine and $OR_2$; $R_2$ is a member selected from the group consisting of alkyl $C_1$–$C_4$, hydroxyalkyl $C_1$–$C_4$ and phenyl.

2. The compound according to claim 1, wherein X is chlorine; $R_1$ is selected from bromine and $OR_2$; $R_2$ is selected from the group consisting of $CH_3$, $C_2H_5$ and $C_2H_4OH$.

3. The compound according to claim 1, α'-bromo-4-chloro-3,5-dinitro-o-xylene.

4. The compound according to claim 1, 4-chloro-2-methyl-3,5-dinitrobenzyl methyl ether.

5. The compound according to claim 1, 4-chloro-2-methyl-3,5-dinitrobenzyl ethyl ether.

6. The compound according to claim 1, 2-(4-chloro-2-methyl-3,5-dinitrobenzyloxy)ethanol.

7. The process for preparing the compound according to claim 1 which comprises: reacting a mixture of concentrated nitric acid and sulfuric acid with 4-chloro-o-toluic acid at a temperature from about 40° C. to about 60° C., reducing resultant 4-chloro-3,5-dinitro-o-toluic acid with diborane, treating resultant 4-chloro-3,5-dinitro-benzyl alcohol with phosphorus tribromide to obtain α'-bromo-4-chloro-3,5-dinitro-o-xylene, reacting the latter with an aliphatic alcohol, and recovering the resultant desired compound.

8. The process according to claim 7 wherein the aliphatic alcohol is methanol.

9. The process according to claim 8 wherein the aliphatic alcohol is ethanol.

10. The process according to claim 9 wherein the alcohol is diethylene glycol.

* * * * *